US007431914B2

(12) United States Patent
Cuthbertson et al.

(10) Patent No.: US 7,431,914 B2

(45) Date of Patent: Oct. 7, 2008

(54) CONTRAST AGENT

(75) Inventors: Alan Cuthbertson, Oslo (NO); Magne Solbakken, Oslo (NO); Dagfinn Lovhaug, Oslo (NO); Philip Duncanson, London (GB); Harry John Wadsworth, Amersham (GB); Anthony Eamon Storey, Amersham (GB); Nigel Anthony Powell, Amersham (GB)

(73) Assignee: GE Healthcare AS, Oslo (NO)

( * ) Notice: Subject to any disclaimer, the term of this patent is extended or adjusted under 35 U.S.C. 154(b) by 204 days.

(21) Appl. No.: 10/559,880

(22) PCT Filed: Nov. 23, 2004

(86) PCT No.: PCT/NO2004/000358

§ 371 (c)(1),
(2), (4) Date: Dec. 7, 2005

(87) PCT Pub. No.: WO2005/049095

PCT Pub. Date: Jun. 2, 2005

(65) Prior Publication Data

US 2006/0193768 A1 Aug. 31, 2006

(30) Foreign Application Priority Data

Nov. 24, 2003 (NO) ................................. 20035228
Jul. 19, 2004 (GB) ................................ 0416062.8

(51) Int. Cl.
*A61K 51/00* (2006.01)

(52) U.S. Cl. .................................................... 424/1.69

(58) Field of Classification Search ................. 424/1.69
See application file for complete search history.

(56) References Cited

U.S. PATENT DOCUMENTS

| | | | | |
|---|---|---|---|---|
| 5,444,069 | A | 8/1995 | Dudley et al. | |
| 5,489,425 | A | 2/1996 | Kruper, Jr. et al. | |
| 6,264,914 | B1 * | 7/2001 | Klaveness et al. | 424/1.65 |
| 7,211,240 | B2 * | 5/2007 | Arbogast et al. | 424/9.1 |
| 2004/0018203 | A1 * | 1/2004 | Pastan et al. | 424/178.1 |

FOREIGN PATENT DOCUMENTS

| | | |
|---|---|---|
| WO | 98/18496 | 5/1998 |
| WO | 03/006070 | 1/2003 |
| WO | 03/006491 | 1/2003 |
| WO | 03/051859 | 6/2003 |
| WO | 2004/062568 | 7/2004 |
| WO | 2005/030266 | 4/2005 |

OTHER PUBLICATIONS

Lehninger Principles of Biochemistry, 3rd edition, 2000, p. 119.*

Turpin, F, et.al. "Synthesis of two novel oxocyclam-binding technetium complexes containing an analogue of cocaine" Journal of Labelled Compounds & Radipharmaceuticals, 2002, vol. 45(5), pp. 379-393 & Chemical Abstracts, abstr No. 137:225697.

Lee, H.S., et.al., "Synthesis of anion receptor grafted siloxane polymers and the ionic conductivity studies of polymer-sald complexes" Journal of the Electrochemical Society, 1999, vol. 146(3), pp. 941-946 & Chemical Abstracts, abstr. No. 130:352967.

Riche, Francoise, et.al., "Niotroimidazoles and hypoxia imaging: synthesis of three technetium-99m complexes bearing a nitroimidazole group: biological results" Bioorganic & Medicinal Chemistry Letters, 2000, Volume Date 2001, vol. 11(1), pp. 71-74 & Chemical Abstracts, abstr No. 134:202049.

GB0416062.8 Search report dated Nov. 25, 2004.

Ponchant, M. et.al. "Radiosynthesis of [tetrazoyl-11C]irbesartan, a non-peptidic angiotensin II antagonist" European Journal of Medicinal Chemistry Editions Scientifique Elsevier, Paris Fr., vol. 32, No. 9, Sep. 1997, pp. 747-752.

Burns, H.D., et.al. "Development of of [11C]L-159,884: A Radiolabelled, Nonpeptide Angiotensin II Antagonist that is Useful for Angiotensin II, At1 Receptor Imaging" Applied Radiation and Isotopes, Pergamon Press Ltd., Exeter, GB, vol. 47, No. 2, Feb. 1996, pp. 211-218.

Int'l Search Report and written opinion PCT/NO2004/000358 dated Nov. 2005.

* cited by examiner

*Primary Examiner*—Michael G. Hartley
(74) *Attorney, Agent, or Firm*—Craig Bohlken

(57) ABSTRACT

A contrast agent of formula I: V-L-R (I) where V is an organic group having binding affinity for an angiotensin II receptor site, L is a linear or branched amino acid-comprising biomodifier or linker moiety, and R is a reporter moiety detectable in in vivo imaging of a human or animal body.

3 Claims, No Drawings

CONTRAST AGENT

This application is a filing under 35 U.S.C. 371 of international application number PCT/NO2004/000358, filed Nov. 23, 2004, which claims priority to application number 20035228 filed Nov. 24, 2003 in Norway and application number 0416062.8 filed Jul. 19, 2004 in Great Britain the entire disclosure of which is hereby incorporated by reference.

FIELD OF INVENTION

The present invention relates to targeted contrast agents suitable for use in diagnostic imaging techniques in which a disease state may be imaged. More specifically the invention relates to contrast agents for the imaging of diseases associated with the up-regulation of the Angiotensin II type receptor $AT_1$. The invention describes ligands designed to have increased potency and optimised excretion and biodistribution profiles compared to existing pharmaceutical preparations.

Diseases which can be detected by the use of a contrast agent targeting the $AT_1$ receptor are congestive heart failure (CHF), atherosclerosis and fibrosis in organs like heart, lungs and liver.

BACKGROUND OF INVENTION

Angiotensin II (Ang II)—the octapeptide (Asp-Arg-Val-Tyr-IIe-His-Pro-Phe)—is a pleiotropic vasoactive peptide that binds to two distinct receptors: the Ang II type 1 ($AT_1$) and type 2 ($AT_2$) receptors. Activation of the renin-angiotensin-aldostrone system (RAAS) results in vascular hypertrophy, vasoconstriction, salt and water retention, and hypertension; These effects are mediated predominantly by $AT_1$ receptors. Paradoxically, other Ang II-mediated effects, including cell death, vasodilation, and natriuresis, are mediated by $AT_2$ receptor activation. The understanding of Ang II signaling mechanisms remains incomplete. $AT_1$ receptor activation triggers a variety of intracellular systems, including tyrosine kinase-induced protein phosphorylation, production of arachidonic acid metabolites, alteration of reactive oxidant species activities, and fluxes in intracellular $Ca^{2+}$ concentrations. $AT_2$ receptor activation leads to stimulation of bradykinin, nitric oxide production, and prostaglandin metabolism, which are, in large part, opposite to the effects of the $AT_1$ receptor. (See: Berry C, Touyz R, Dominiczak A F, Webb R C, Johns D G.: Am J Physiol Heart Circ Physiol. 2001 December; 281(6):H2337-65. Angiotensin receptors: signaling, vascular pathophysiology, and interactions with ceramide).

Ang II is the active component of the renin-angiotensin-aldosterone system (RAAS). It plays an important physiological role in the regulation of blood pressure, plasma volume, sympathetic nervous activity, and thirst responses. Ang II also has a pathophysiological role in cardiac hypertrophy, myocardial infarction, hypertension, chronic obstructive pulmonary disease, liver fibrosis and atherosclerosis. It is produced systemically via the classical RAAS and locally via tissue RAAS. In the classical RAAS, circulating renal-derived renin cleaves hepatic-derived angiotensinogen to form the decapeptide angiotensin I (Ang I), which is converted by angiotensin-converting enzyme (ACE) in the lungs to the active Ang II. Ang I can also be processed into the heptapeptide Ang-(1-7) by tissue endopeptidases. The RAAS system is illustrated schematically in FIG. 1 hereto which is based on FIG. 1 in the article by Foote et al. in Ann. Pharmacother. 27: 1495-1503 (1993).

In addition to the RAAS playing an important role in the normal cardiovascular homeostasis, over activity of the RAAS has been implicated in the development of various cardiovascular diseases, such as hypertension, congestive heart failure, coronary ischemia and renal insufficiency. After myocardial infarction (MI), RAAS becomes activated. Specifically the $AT_1$ receptor seems to play a prominent role in post-MI remodelling, since $AT_1$ receptor expression is increased after MI and in left ventricular dysfunction. Therefore drugs that interfere with RAAS, such as ACE inhibitors and $AT_1$ receptor antagonists, have been shown to be of great therapeutic benefit in the treatment of such cardiovascular disorders.

For heart, kidneys, lungs and liver alike, fibrosis represents a common pathway to their failure. Understanding pathophysiologic mechanisms involved in organ fibrosis is therefore of considerable interest, particularly given the potential for protective pharmacological strategies. Tissue repair involves inflammatory cells, including members of the monocyte/macrophage lineage, integral to initiating the repair process; and myofibroblasts, phenotypically transformed interstitial fibroblasts, responsible for collagen turnover and fibrous tissue formation. Each of these cellular events in the microenvironment of repair are associated with molecular events that lead to the de novo generation of angiotensin II (Ang II). In an autocrine/paracrine manner, this peptide regulates expression of TGF-beta 1 via angiotensin ($AT_1$) receptor-ligand binding. It is this cytokine that contributes to phenotypic conversion, of fibroblasts to myofibroblasts (myoFb) and regulates myofibroblast turnover of collagen. Angiotensin-converting enzyme (ACE) inhibition or $AT_1$ receptor antagonism each prevent many of these molecular and cellular responses that eventuate in fibrosis and therefore have been found to be protective interventions. (See: Weber K T. Fibrosis, a common pathway to organ failure: angiotensin II and tissue repair. Semin Nephrol. 1997 September; 17(5): 467-91 and references therein).

Ang II may regulate tissue fibrosis via the activation of mesenchymal cells. For example, Ang II stimulates the proliferation of cardiac fibroblasts in vitro via activation of $AT_1$. The presence of $AT_1$ receptors has also been demonstrated on cardiac fibroblasts in vitro. Most of the profibrotic effects of Ang II appear to be mediated via this receptor; however, increased $AT_2$ expression on cardiac fibroblasts has been detected in hypertrophied human heart, and the balance between the expression of these two subtypes may be critical in determining the response to Ang II. (See: Am. J. Respir. Crit. Care Med., Volume 161, Number 6, June 2000, 1999-2004. Angiotensin II Is Mitogenic for Human Lung Fibroblasts via Activation of the Type 1 Receptor Richard P. Marshall, Robin J. McAnulty, and Geoffrey J. Laurent and references therein).

The Ang II receptors can be distinguished according to inhibition by specific antagonists. $AT_1$ receptors are selectively antagonized by biphenylimidazoles, such as Losartan, whereas tetrahydroimidazopyridines specifically inhibit $AT_2$ receptors. The $AT_2$ receptor may also be selectively activated by CGP-42112A. This is a hexapeptide analog of Ang II, which may also inhibit the $AT_2$ receptor, depending on concentration). Two other angiotensin receptors have been described: $AT_3$ and $AT_4$ subtypes.

In rodents, the $AT_1$ receptor has two functionally distinct subtypes, $AT_{1A}$ and $AT_{1B}$, with >95% amino acid sequence homology.

The second major angiotensin receptor isoform is the $AT_2$ receptor. It has low amino acid sequence homology (~34%) with $AT_{1A}$ or $AT_{1B}$ receptors. Although the exact signaling pathways and the functional roles of $AT_2$ receptors are unclear, these receptors may antagonize, under physiological conditions, $AT_1$-mediated actions inhibiting cell growth and by inducing apoptosis and vasodilation. The exact role of $AT_2$ receptors in cardiovascular disease remains to be defined.

Other receptors for Ang II besides $AT_1$ and $AT_2$ are known and are generally referred to as $AT_{atypical}$ (see Kang et al., Am. Heart J. 127: 1388-1401 (1994)). The suppression of Ang II's effects has been used therapeutically, for example in the management of hypertension and heart failure. This has been achieved in a number of ways: by the use of renin inhibitors which block the conversion of angiotensinogen to angiotensin I (the precursor to Ang II); by the use of angiotensin converting enzyme (ACE) inhibitors that block the conversion of angiotensin I to Ang II (and also block bioconversion of bradykinin and prostaglandins); by the use of anti-Ang II-antibodies; and by the use of Ang II-receptor antagonists.

Beta blockers are most commonly used in treatment of arrhythmias. Anti-arrhythric drugs have had limited overall success and calcium channel blockers can sometimes induce arrhythmias. No single agent shows superiority, with the possible exception of amiodarone. Short-term anti-arrhythmic benefit has been found to be offset by, depending on the specific drug, neutral or negative effects on mortality (Sanguinetti M C and Bennett, P B: Anti-arrhythmic drug target choices and screening. Circulation 2003, 93(6): 491-9257-263). Clearly better anti-arrhythmic drugs are needed.

A publication in Lancet (Lindholm, L H et al. Effect of Losartan on sudden cardiac death in people with diabetes: data from the LIFE study. The Lancet, 2003, 362: 619-620) revealed that $AT_1$ receptor antagonists in addition of being generally favourable to patients with CHF, also reduce the incidence of sudden cardiac death. There exist a few studies showing that $AT_1$ antagonists have an anti-arrhythmia effect on arrhythmias induced by myocardial infarct or in reperfusion after ligation of LAD (Harada K et al. Angiotensin II Type 1*a* Receptor is involved in the occurrence of reperfusion arrhythmias. Circulation. 1998, 97:315-317. Ozer M K et al. Effects of Captopril and Losartan on myocardial ischemia-reperfusion induced arrhythmias and necrosis in rats. Pharmacological research, 2002, 45 (4), 257-263 Lynch J J et al. EXP3174, the AII antagonist human metabolite of Losartan, but not Losartan nor the Angiotensin-converting enzyme inhibitor captopril, prevents the development of lethal ischemic arrhythmias in a canine model of recent myocardial infarction. JACC, 1999, 34 876-884).

It has now been found that it is possible to image Ang II receptor sites in vivo using targeted contrast agents in which the targeting binding ligand has affinity for Ang II-receptor sites. The Ang II receptors are generally accessible to such contrast agents when they are administered into the blood stream. Accordingly, using such targeted contrast agents it is possible to detect diseases and disorders such as heart failure, atherosclerosis and restricted blood flow, as well as other vascular diseases and disorders, and also to monitor the progression of treatment for such diseases and disorders.

DESCRIPTION OF RELATED ART

WO 98/18496 (Nycomed Imaging AS) discloses contrast agents comprising Ang II-receptor antagonists labelled for in vivo imaging.

U.S. Pat. No. 5,138,069 discloses substituted imidazoles for use as Ang II receptor blockers. Further, U.S. Pat. No. 5,264,581 (Cariani) discloses radioiodinated imidazole Ang II antagonists.

SUMMARY OF THE INVENTION

When using imidazoles, e.g. Losartan, as the binding ligand in a conjugate with a relatively large reporter, such as a bulky chelate, the affinity of the ligand for the selected binding site may be negatively affected.

A problem with agents like Losartan, both the drug and the chelate conjugate, is that they excrete mainly (more than 80%) through the liver and have an affinity (Ki) which is less avid than the natural hormone Ang II. This constitutes two problems in the use of such compositions as targeting contrast agents: Firstly a small amount of the administered composition is allowed to bind to the Ang II receptor site before it is absorbed in the liver and secondly the liver up-take results in increased background activity e.g. the background from the liver may interfere with imaging of diseased areas of the heart.

It has now been found that the introduction of an amino acid-comprising biomodifier/linker between the targeting ligand and the chelate or reporter moiety can reduce the liver up-take and can also increase the binding affinity to Ang II receptor sites. The biomodifier/linker may be linear or branched. Hence, compositions of matter of the present invention are useful diagnostic contrast agents for in vivo imaging of the mammalian body. Furthermore, the patients undergoing the imaging procedure may also be on 'sartan' drug therapy. 'Sartans' e.g. Losartan are Ang II receptor antagonists used in treatment of hypertension. A contrast agent targeting Ang II receptors will experience a competition with the treatment drug for binding to the same receptor site. It is therefore considered desirable to develop contrast agents possessing higher affinity for the $AT_1$ receptor than the prescribed drug to avoid deleterious competition effects of the cold drug i.e. the prescribed non-detectable 'sartan' drug.

The in vivo detectable moiety (reporter) can be any moiety capable of detection either directly or indirectly in an in vivo-diagnostic imaging procedure e.g. by MRI, optical imaging, scintigraphy, SPECT, PET, X-ray, ultrasound, electrical impedance or magnetometric procedures.

The compositions of matter of the present invention are useful for the in vivo diagnostic imaging of a range of disease states (congestive heart failure (CHF), atherosclerosis, fibrosis in organs like heart, lungs and liver) where the up regulation of Ang II receptor sites is known to be involved.

DETAILED DESCRIPTION OF THE INVENTION

In a first aspect the present invention provides a composition of matter of formula I $$V\text{-}L\text{-}R \qquad (I)$$

where V is an organic group having binding affinity for an angiotensin II receptor site, L is an amino acid-comprising biomodifier or linker moiety, and R is a moiety detectable in an in vivo imaging procedure of a human or animal body.

The ligand V may be any organic compound having affinity for Ang II receptors. Compounds having a marked affinity for particular types of Ang II receptors, such as $AT_1$ or $AT_2$, are generally preferred. Imidazole Ang II aentagonist ligands are preferred and most preferred are ligands such as Losartani, Valsartan, Candesartan and Eprosartan.

For contrast agents useful in diagnosis and particularly in in vivo diagnosis the moiety R must be able to carry the imageable moiety or moieties denoted M. By carrying is meant any form of association between the moiety R and M such as a chemical bond, e.g. covalent bond or electrovalent or ionic bonds or by absorption, or any other type of association. R can be any imageable moiety. Where M is a metal entity then $Y_1$ represents a chelating agent. The nature of R and/or $Y_1M$ will depend of the imaging modality utilised in the diagnosis. R and/or $Y_1M$ must be, capable of detection either directly or indirectly in an in vivo diagnostic imaging procedure, and comprise e.g. moieties which emit or may be caused to emit detectable radiation,(epg. by radioactive decay, fluorescence excitation, spin resonance excitation, etc.), moieties which affect local electromagnetic fields (eg. paramagnetic, superparamagnetic, ferrimagnetic or ferromagnetic species), moieties which absorb or scatter radiation energy (eg. chromophores, particles (including gas or liquid containing vesicles), heavy elements and compounds thereof, etc.), and moieties which generate a detectable substance (eg. gas microbubble generators).

In a preferred embodiment one moiety R is covalently bound directly to L forming an N-alkyl glycine unit.

Chelating agents of formula (II) and (e) hereinafter are also particularly preferred.

A wide range of suitable imageable moieties are known from e.g. WO 98/18496, the content of which is incorporated by reference.

Imaging modalities and imageable moieties R and M are described in more detail hereinafter:

In a first embodiment, the compound of formula (I) comprises a moiety $Y_1$ carrying one or more imageable moieties M useful in the Radio and SPECT imaging modality. Preferably M is a gamma emitter with low or no alpha- and beta-emission and with a half-life of more than one hour. Preferred groups M are the radionuclides $^{67}Ga$, $^{111}In$, $^{123}I$, $^{125}I$, $^{131}I$, $^{81m}Kr$, $^{99}Mo$, $^{99m}Tc$, $^{201}TI$ and $^{133}Xe$. Most preferred is $^{99m}Tc$.

M can further be represented by the following isotopes or isotope pairs for use both in imaging and therapy without having to change the radiolabeling methodology or chelator: $^{47}Sc_{21}$; $^{141}Ce_{58}$; $^{188}Re_{75}$; $^{177}Lu_{71}$; $^{199}Au_{79}$; $^{47}Sc_{21}$; $^{131}I_{53}$; $^{67}Cu_{29}$; $^{131}I_{53}$ and $^{123}I_{53}$; $^{188}Re_{75}$ and $^{99m}Tc_{43}$; $^{90}Y_{39}$; $^{47}Sc_{21}$ and $^{87}Y_{39}$; $^{47}Sc_{21}$ and $^{44}Sc_{21}$; $^{90}Y_{39}$ and $^{123}I_{53}$; $^{146}Sm_{62}$ and $^{153}Sm_{62}$; and $^{90}Y_{39}$ and $^{111}In_{49}$.

When M denotes a metallic radionuclide then $Y_1$ denotes a chelating agent suitable for forming a stable chelate with M. Such chelating agents are well known from the state of art and typical examples of such chelating agents are described in Table I of WO 01/77145.

Particularly preferred are chelating agents of formula (II):

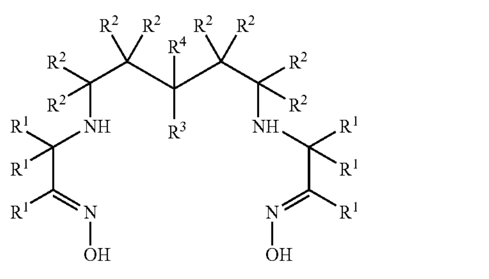

wherein:

each $R^1$, $R^2$, $R^3$ and $R^4$ is independently H or $C_{1-10}$ alkyl, $C_{3-10}$ alkylaryl, $C_{2-10}$ alkoxyalkyl, $C_{1-10}$ hydroxyalkyl, $C_{1-10}$ alkylamine, $C_{1-10}$ fluoroalkyl, or 2 or more R groups, together with the atoms to which they are attached form a carbocyclic, heterocyclic, saturated or unsaturated ring.

More particularly preferred are chelating agents of formula (II) where $R^1$, $R^2$ and $R^3$ are hydrogen or methyl groups and $R^4$ is an alkylamine group, most specifically a compound of formula (e), herein denoted cPN216. For the following structures the asterisks denote possible linking sites. For formula (e) the asterisk denotes an amine group.

Formula (e)

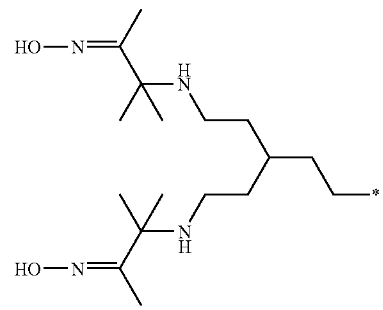

Most preferred for $Y_1$ is when the chelate is cPN216 and when the imaging moiety M is $^{99m}Tc$.

Other preferred chelating agent can be represented by formulas a, b, c and d.

a

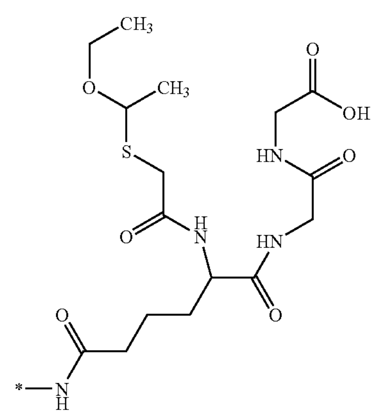

b

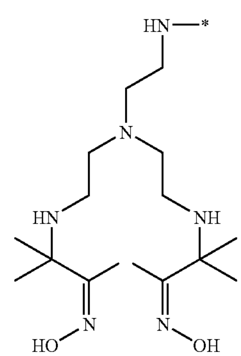

-continued c

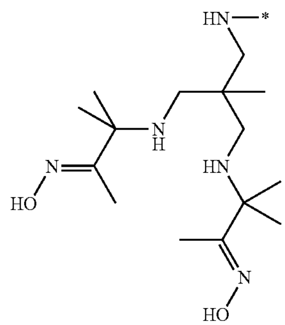

d

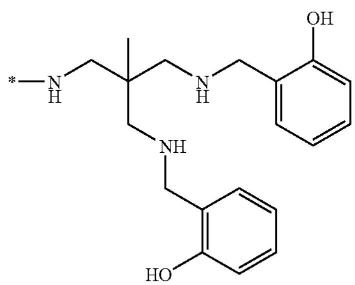

Synthesis of chelating agents of formula (II) and (e) are described in WO 03/006070.

Other relevant chelating agents are of formula (III)

(III)

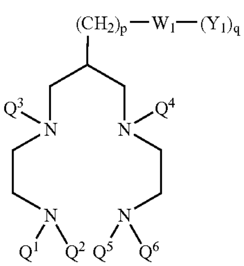

wherein $Q_1$-$Q_6$ are independently Q groups, where Q is H, alkyl, aryl or an amine protecting group, $W_1$ is —NR—, —$CO_2$—, —CO—, —NR(C═S)—, —NR(C═O)—, —CONR— or a Q group;

each Y is independently a D- or L-amino acid, —$CH_2$—, —$CH_2OCH_2$— or —$OCH_2CH_2O$— or a $W_1$ group;

p is an integer of value 1 to 8;

q is an integer of value 0 to 30;

R is H, $C_{1-4}$ alkyl, $C_{2-4}$ alkoxyalkyl, $C_{1-4}$ hydroxyalkyl, or $C_{1-4}$ fluoroalkyl;

Synthesis of tetraamin chelating agents of formula (III) can be found in GB patent application number GB 0416062.8.

Non-metal radionuclides such as $^{123}I$, $^{125}I$ and $^{131}I$ may be covalently linked to the moiety L by a substitution or addition reaction well known from the state of art.

In a second embodiment, the compound of formula (I) comprises a moiety R useful in the PET imaging modality. R then denotes a radioemitter with positron-emitting properties. Preferred groups R are the radionuclides $^{11}C$, $^{18}F$, $^{68}Ga$, $^{13}N$, $^{15}O$ and $^{82}Rb$. $^{18}F$ is specifically preferred. The metallic radioemitters $^{82}Rb$ and $^{68}Ga$ chelated with a chelating agent $Y_1$ are also preferred.

Thiol coupling chemistry, $^{18}F$-sypthons and labelled peptides prepared using the thiol coupling chemistry are described in WO 03/080544, the content of which is incorporated herein by reference.

Description of peptides labelled by use of thiol coupling chemistry can be found in GB patent application no. 0317815.9, the content of which is incorporated herein by reference.

When M denotes a metallic radionuclide then $Y_1$ denotes a chelating agent suitable for forming a stable chelate with M. Such chelating agents are well known from the state of art and typical examples of such chelating agents are described in Table I of WO 01/77145 and to the previous part on Radio and SPECT imaging.

In another preferred embodiment $Y_1$ is the DOTA chelating agent and M is $^{68}Ga$ which can be readily introduced in to the chelate using microwave chemistry.

Non-metal radionuclides such as $^{18}F$ may be covalently linked to the moiety L by a substitution or addition reaction well known from the state of art and also described eg. in WO03/080544 which is hereby incorporated by reference.

In a third embodiment, R of the compound of formula (I) comprises a moiety $Y_1$ carrying one or more imageable moieties M useful in the MR imaging modality. M here denotes a paramagnetic metal such those mentioned in U.S. Pat. No. 4,647,447, $Gd^{3+}$, $Dy^{3+}$, $Fe^{3+}$ and $Mn^{2+}$ are particularly preferred and $Y_1$ denotes a chelating agent, in particular a chelating agent such as acyclic or cyclic polyaminocarboxylates (e.g. DTPA, DTPA-BMA, DOTA and DO3A),as described e.g. in U.S. Pat. No. 4,647,447 and WO 86/02841. M may also denote metal oxides such as superparamagnetic, ferrimagnetic or ferromagnetic species which are absorbed by R, e.g. such that R functions as a coating to the metal oxide. Metal oxides for use as MR contrast agents are described e.g. in U.S. Pat. No. 6,230,777 which is hereby incorporated by reference.

In a fourth embodiment R of the compound of formula (I) comprises a moiety $Y_1$ carrying one or more imageable moieties M useful in the X-ray imaging modality. M here denotes a heavy metal such as W, Au and Bi preferably in the form of oxides which may be absorbed to R. R can also be represented by lodinated aryl derivatives particularly well known as X-ray contrast agents, e.g. lopamiron™ and Omnipaque™. These agents can e.g. be linked via a amide or amine function to V of formula (I).

In a further embodiment the compound of formula (I) comprises R in the form of gas filled microvesicles. Such ultrasound imaging agents can be utilised in the imaging of receptors e.g. when they are functionalised for binding to a peptide as described in the state of art e.g. in WO98/18500.

In a sixth embodiment of the present invention the moiety R of formula (I) may be any moiety capable of detection either directly or indirectly in an optical imaging procedure. The detectable moiety can be a light scatterer (e.g. a coloured or uncoloured particle), a light absorber or a light emitter. More preferably R is represented by a dye such as a chromophore or a fluorescent compound. The moiety R can be any dye that interacts with light in the electromagnetic spectrum with wavelengths from the ultraviolet light to the near-infrared. In a preferred version R has fluorescent properties.

Preferred organic dye moieties include groups having an extensive delocalized electron system, eg. cyanines, merocyanines, indocyabines, phthalocyanines, naphthalocyanines, triphenylmethines, porphyrins, pyrilium dyes, thiapyrilium dyes, squarylium dyes, croconium, dyes, azulenium dyes, indoanilines, benzophenoxazinium dyes, benzothiaphenothiazinium dyes, anthraquinones, napthoquinones, indathrenes, phthaloylacridones, trisphenoquinones, azo dyes, intramolecular and intermolecular charge-transfer dyes and dye complexes, tropones, tetrazines, bis(dithiolene) complexes, bis(benzene-dithiolate) complexes, iodoaniline dyes, bis(S,O-dithiolene) complexes. Fluorescent proteins, such as green fluorescent protein (GFP) and modifications of GFP that have different absorption/emission properties are also useful. Complexes of certain rare earth metals (e.g., europium, samarium, terbium or dysprosium) are used in certain contexts, as are fluorescent nanocrystals (quantum dots).

Further descriptions of moieties suitable in optical imaging procedures are found in Norwegian patent application no. 200303115 the content of which is hereby incorporated by reference.

The invention may be exemplified by Losartan derivatives and is based on attachment of biomodifier/linker and reporter moieties to the imidazol 5-position. The principle also applies to other compounds having structural similarities, e.g. Valsartan, Candesartan and Eprosartan, possessing suitable anchoring sites in the part of the molecule corresponding to the Losartan imidazole ring.

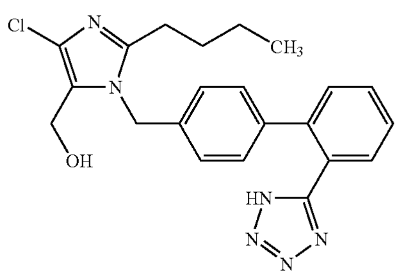

Losartan

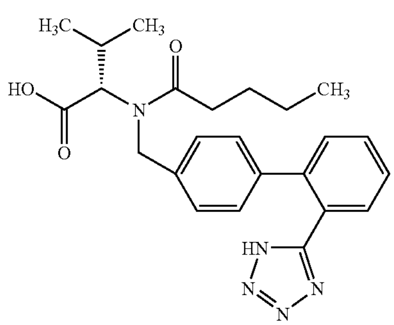

Valsartan

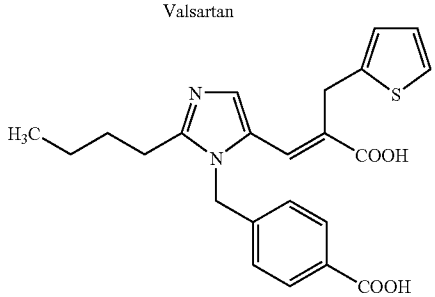

Eprosartan

-continued

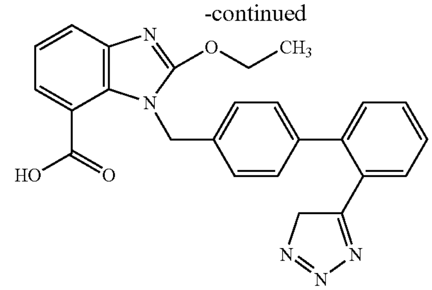

Candesartan

One role of the biomodifier/linker moiety L may be to distance a relatively bulky reporter, such as a metal complex, from the active site of the binding ligand V. The biomodifier/linker moiety can be selected to increase the binding affinity of the composition for the receptor. The biomodifier/linker moiety comprises 1-40 amino acids, and preferred 1-20 amino acids, and more preferred 1-10 amino acids and most preferred 1-5 amino acids. Further the biomodifier/linker moiety may comprise one or more dicarboxylic acid units (e.g. diglycoloyl units, glycolyl units, succinyl, glutaryl units), ethyleneglycol units, diamines, PEG or PEG like units or combinations of the above.

The nature of the linker group can also be used to modify the biodistribution of the resulting metal complex of the conjugate e.g. the introduction of amino acids with different properties can decrease the liver up-take.

Some of the compounds of the present invention have high affinity for the $AT_1$ receptor. "High affinity" refers to compounds having a Ki≦5 nM and preferably <0.1 nM and most preferred Ki's in the pM or sub pM range calculated from competitive binding assays for $AT_1$ and where the Ki value was determined by competition with the known high affinity vector $^{125}$I-$Sar_1Ile_8$-angiotensin II. The Ki for Ang II in this assay system is around 5 nM.

Ang II-receptor antagonists derived from the so called 'sartan' class of drugs such as Valsartan, Candesartan and Eprosartan and preferably Losartan, labelled with an imaging moiety are useful diagnostic imaging agents for in vivo imaging of a human or animal body.

One preferred embodiment of the invention is the $^{99m}$Tc labelled contrast agents $^{99m}$Tc (Losartan-Leu-diglycolyl-cPn216), $^{99m}$Tc (Losartan-Leu-Gly-diglycolyl-cPn216), $^{99m}$Tc (Losartan-Leu-β-Ala-diglycolyl-cPn216) and $^{99m}$Tc (Losartan-Leu-Lys(Propionyl-PEG(12)-Ac)-Diglycoloyl-cPn216).

The contrast agent of formula (I) are preferably administered as a pharmaceutical formulation comprising the compound of formula (I) in a form suitable for administration to a mammal, such as a human. The administration is suitable carried out by injection or infusion of the formulation such as an aqueous solution. The formulation may contain one or more pharmaceutical acceptable additives and/or excipients e.g. buffers; solubilisers such as cyclodextrins; or surfactants such as Pluronic, Tween or phospholipids. Further, stabilisers or antioxidants such as ascorbic acid, gentisic acid or para-aminobenzoic acid and also bulking agents for lyophilisation such as sodium chloride or mannitol may be added.

The present invention also provides a pharmaceutical composition comprising an effective amount (e.g. an amount effective for enhancing image contrast in an in vivo imaging procedure) of a composition of general formula I or a salt thereof, together with one or more pharmaceutically acceptable adjuvants, excipients or diluents.

Viewed from a further aspect the invention provides the use of a composition of formula I for the manufacture of a contrast medium for use in a method of diagnosis involving administration of said contrast medium to a human or animal body and generation of an image of at least part of said body.

Viewed from a still further aspect the invention provides a method of generating enhanced images of a human or animal body previously administered with a contrast agent composition comprising a composition of matter as defined by formula I, which method comprises generating an image of at least part of said body.

The invention further provides a method for the monitoring of the effect of treatment of heart failure and other diseases associated with up-regulation of the $AT_1$ receptor.

In still another aspect the invention provides a kit for the preparation of a radiopharmaceutical composition of formula (I) comprising a ligand-chelate conjugate and a reducing agent. Preferably the reducing agent is a stannous salt. The kit may further comprise one or more stabilisers, antioxidants, bulking agents for lyophilisation and solubilisers.

The three letter abbreviations used herein for the amino acids have the following meaning:

| | |
|---|---|
| Ala | Alanine |
| Asp | Aspartic acid |
| Arg | Arginine |
| Glu | Glutamic acid |
| Gly | Glycine |

-continued

| | |
|---|---|
| Lys | Lysine |
| Leu | Leucine |
| Sar | Sarcosine |
| Val | Valine |
| Tyr | Tyrosine |
| Ile | Isoleucine |
| His | Histidine |
| Pro | Proline |
| Phe | Phenylalanine |
| Nal | 2-Amino-3-naphtyl propionic acid |
| Cha | 2-Amino-3-cyclohexyl propionic acid |

The meaning of other abbreviations used herein is as follow:

| | |
|---|---|
| DOTA | 1,4,7,10-tetraazacyclododecan-1,14,7,10-tetraacetic acid |
| PEG | polyethyleneglycol |
| DIEA | diisopropylethylamine |
| DPPA | diphenylphosphoryl azide |
| DBU | 1,8-diaza-bicyclo (5,4,0) undec-7-ene |
| DMF | dimethyl formamide |
| MDP | methylene diphosphonate |
| TFA | trifluoroacetic acid |
| THF | tetrahydro furan |
| HATU | N-[(dimethylamino)-1H-1,2,3-triazolo [4,5-b]pyridino-1-ylmethylene]-N-methylmethanaminium hexafluorophosphonate N-oxide |
| PyAOP | 7-Azabenzotriazol-1-yloxytris(pyrrolidino)phosphonium-hexafluorophosphate |
| Fmoc | 9-fluorenylmethoxycarbonyl |

General Procedures

Scheme 1 shows the solid phase synthesis of Losartan linker chelating agent conjugate. The circle donates a solid support particle.

Scheme 1

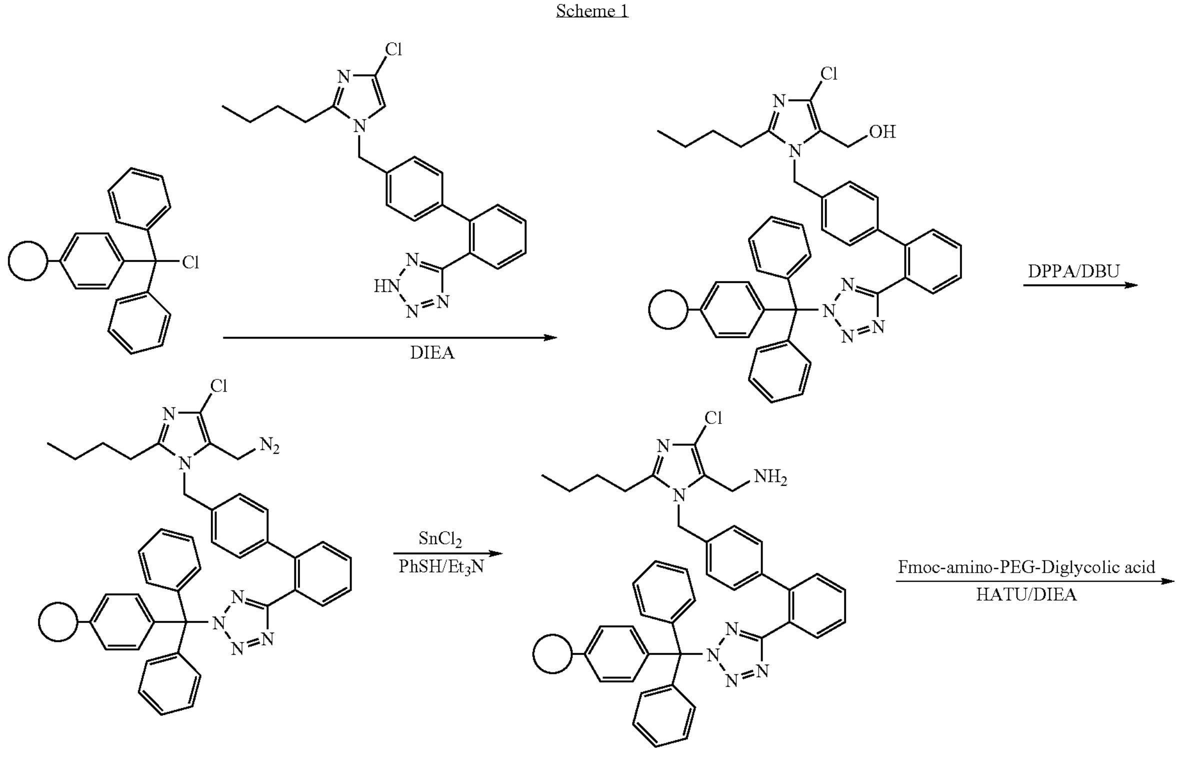

-continued
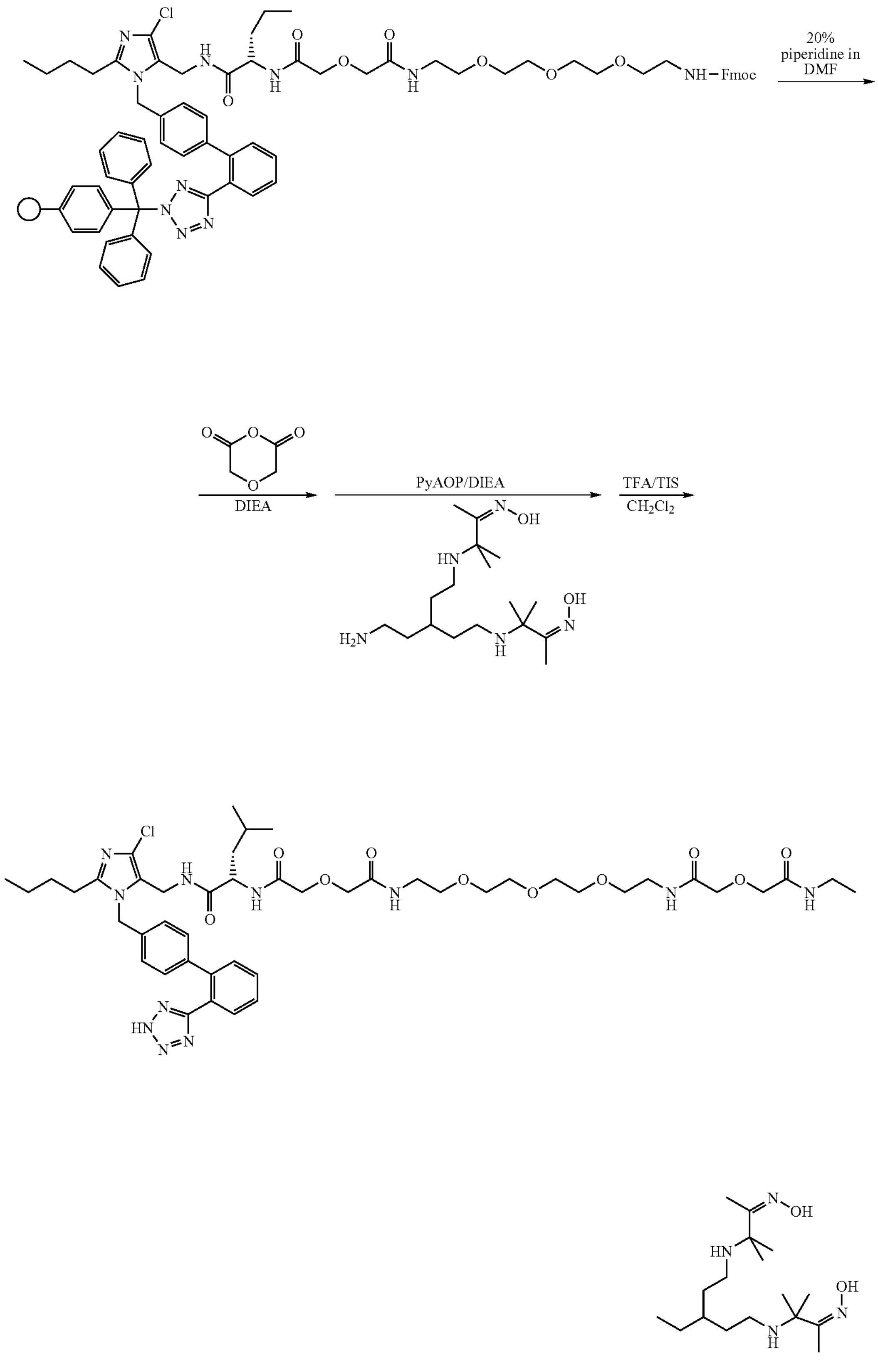

$K_i$ Determination

The affinity of the compounds was determined as the dissociation constant ($K_d$) and measured by displacement of a radiolabelled ligand of known affinity.

The affinity of the compound for the $AT_1$ receptor has been determined in a competition assay using membranes from CHO cells expressing the receptor. Binding of $^{125}$I-Sar$_1$-IIe$_8$-Angiotensin II, a ligand known to bind very efficiently to $AT_1$ receptors, was competed with various concentrations of the test substance. The $K_i$ is the concentration of the competing ligand in the competition assay which would occupy 50% of the receptors if no radoligand was present. $K_i$ is calculated using the Cheng-Prussoff equation:

$$K_i = IC_{50}/(1+(L)/K_d)$$

Where (L) is the concentration of the radiolabelled ligand used and the Kd is the dissociation constant of the radiolabelled ligand for the receptor. $IC_{50}$ is the concentration of competing ligand which displaces 50% of the specific binding of the radioligand. The $IC_{50}$ value for a compound may vary between experiments depending on the radioligand concentration, whereas the $K_i$ is an absolute value.

$^{99m}$Tc-Labelling Protocol

A preparation is made by dissolving 0.1 mg freeze-dried cPn216 derived compound in 0.2 ml (distilled and oxygen-free) water. This solution is transferred into a 10 ml nitrogen filled vial. 0.5 ml carbonate buffer, 0.5 ml Na$^{99m}$TcO$_4$ solution and 0.1 ml Sn-MDP solution are added. The preparation is left at room temperature for 20 minutes. Carbonate buffer: The carbonate buffer has a pH of 9.2 and contains 8.4 mg $NaHCO_3$ and 10.6 mg $Na_2CO_3$ per ml water. It is purged with nitrogen gas for at least 15 minutes before use.

Na$^{99m}$TcO$_4$ solution: Technetium generator (e.g. Ifetec generator) eluate, diluted to a radioactive concentration: of 2 GBq/ml, oxygen free.

Sn-MDP solution: This solution contains 0.131 mg $SnCl_2*2H_2O$ and 0.925 mg MDP (methylene diphosphonate) per ml water. The solution is made freshly before use under continuous nitrogen gas purging.

EXAMPLES

Example 1

Losartan-Leu Derivatised with cPn216 via a Short PEG-Linker (Solid Phase Synthesis)

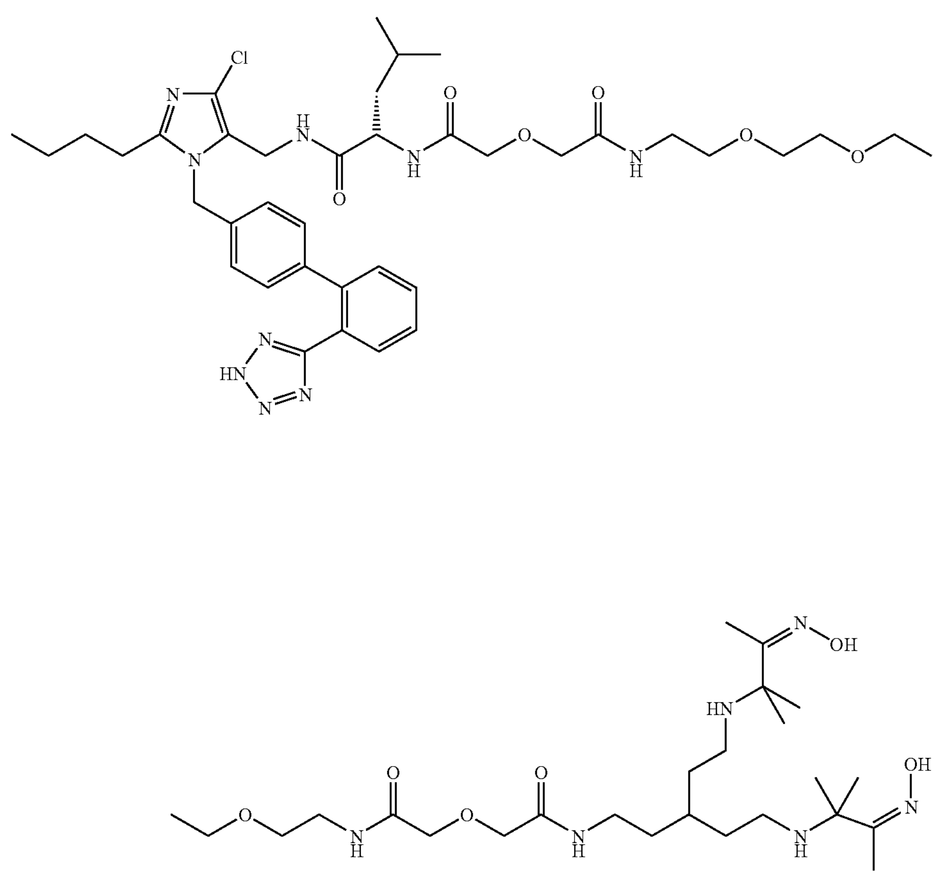

All reactions were carried out in a manual nitrogen bubbler apparatus.

a) Attachment of Losartan to Trityl Derivatised Solid Support

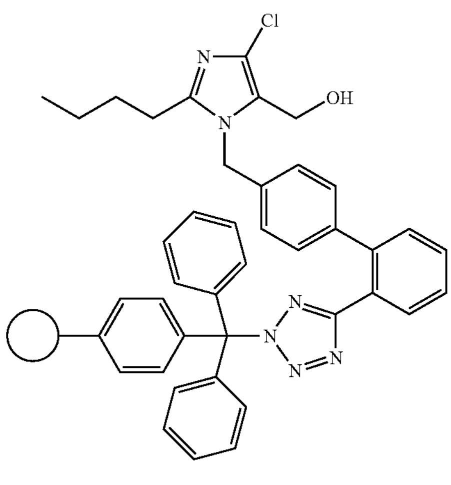

Losartan (MSD, 0.236 g, 0.558 mmol) and triethylamine (Fluka, 0.233 ml, 1.67 mmol) were added to a suspension of trityl chloride resin (Novabiochem, susbstitution 1.24 mmol/g, 0.300 g) in DMF (5 ml). After 4 days the resin was drained and washed. An aliquot of the resin was cleaved. (dichloromethane/TFA/triisopropylsilane, 92.5: 5.0: 2.5, 15 min). HPLC analysis (column Phenomenex Luna C18(2) 3 μm 4.6×50 mm, solvents: A=water/0.1% TFA and B=acetonitrile/0.1% TFA; gradient 10-40% B over 10 min; flow 2.0 ml/min, UV detection at 214 and 254 nm) gave a peak with $t_R$ 6.7 minutes corresponding to losartan. The resin was treated with dichloromethane/methanol/diisopropylethylamine solution (17:2:1, 20 ml, 1 h), washed with dichloromethane and dried.

b) Replacement of the Hydroxyl Group by Azide

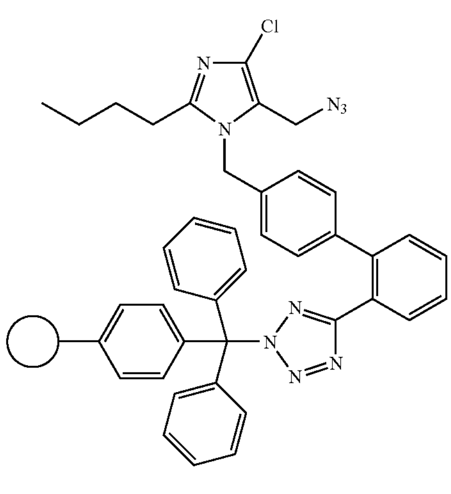

Diphenylphosphoryl azide (Aldrich, 0.481 ml, 2.23 mmol) and DBU (0.611 ml, 4.09 mmol) were added to a suspension of resin bound losartan from a) (0.372 mmol) in THF (10 ml). The reaction was left over night. An aliquot of the resin was cleaved as described under a). Analysis by LC-MS (column Phenomenex Luna C18(2) 3 μm 50×4.60 mm, solvents: A=water/0.1% TFA and B=acetonitrile/0.1% TFA; gradient 20-80% B over 10 min; flow 1 ml/min, UV detection at 214 nm, ESI-MS) gave a peak, $t_R$ 7.3 minutes, with m/z 448.1 ($MH^+$) corresponding to the structure.

c) Reduction of the Azide Group to Amine

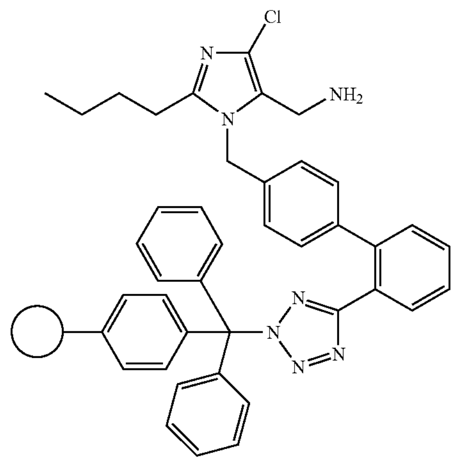

To a suspension of the resin from b) in THF (4 ml) was added addition of tin(II)chloride (Acros, 0.141 g, 0.744 mmol), thiophenol (Fluka, 0.304 ml, 2.976 mmol) and triethylamine (Fluka, 0.311 ml, 2.23 mmol). After 1.5 hour an aliquot of the resin was cleaved as described under a). LC-MS analysis (column Phenomenex Luna C18(2) 3 μm 50×4.60 mm, solvents: A=water/0.1% TFA and B=acetonitrile/0.1% TFA; gradient 20-80% B over 10 min; flow 1 ml/min, UV detection at 214 nm, ESI-MS) gave a peak at 1.9 minutes with m/z 422.2 ($MH^+$) as expected for amine.

d) Losartan-Leu-Diglycoloyl-PEG(4)-Diglycolyl-cPn216

Fmoc-Leu-OH (Novabiochem, 0.030 g, 0.084 mmol) and Fmoc-amino PEG diglycolic acid (Polypure, 0.045 mg, 0.084 mmol) were successively coupled to an aliquot of the resin bound amino-losartan from c) (0.042 mmol) in DMF using standard coupling reagents (HATU and DIEA) and standard Fmoc-cleavage protocol (20% piperidine in DMF). Completion of couplings were checked by standard Kaiser test. The second diglycoloyl unit was introduced using diglycolic anhydride (Aldrich, 0.010 g, 0.084 mmol) and DIEA (0.014 ml, 0.084 mmol). To the resin (containing a terminal carboxyl function) was added the chelate cPn216 (0.029 g, 0.084 mmol), PyAOP (Applied Biosystems, 0.022 g, 0.042 mmol) and DIEA (0.014 ml, 0.084 mmol). After two hours the compound was cleaved off the resin (dichloromethane/TFA/triisopropylsilane, 92.5: 5.0: 2.5 solution for 30 minutes). The solution was filtered, concentrated and purified by preparative, HPLC (column Phenomenex Luna C18(2) 5 μm 10.0×250 mm, solvents: A=water/0.1% TFA and B=acetonitrilB/0.1% TFA; gradient 25-30% B over 60 min; flow 5.0 ml/min, UV detection at 214 nm) to give 3 mg of product after lyophilisation. LC-MS analysis (column Phenomenex Luna C18

(2) 3 μm 50×4.60 mm, solvents: A=water/0.1% TFA and B=acetonitrile/0.1% TFA; gradient 10-80% B over 10 min; flow 0.3 ml/min, UV detection at 214 and 254 nm, ESI-MS) $t_R$ 5.9 minutes, m/z 1266.5 ($MH^+$)) confirmed the structure.

The compound was tested in vitro for binding to angiotensin-II receptor AT1 (Ki 0.5 nM).

Examples 2-18

Amino Acid Substituted Losartan Derivatives

Amino derivatives of the general formula (IV) listed in Table 1 were synthesised on solid support as described in Example 1. The products were purified by reverse phase chromatography (Phenomenex Luna C18(2) columns) using suitable gradients of acetonitrile/water containing 0.1% TFA and were analysed by LC-MS using electrospray Ionisation.

TABLE I (IV)

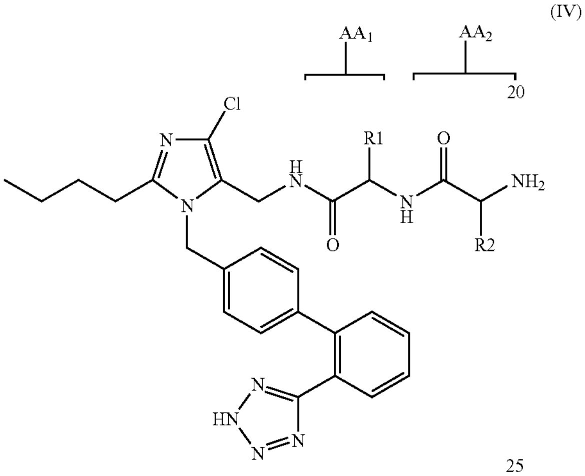

| AA1 | AA2 | MW (exact) | $MH^+$ observed |
|---|---|---|---|
| Lys | | 549.27 | 550.2 |
| Glu | | 550.22 | 551.1 |
| Leu | | 534.26 | 535.1 |
| D-Lys | | 549.27 | 550.2 |
| D-Glu | | 550.22 | 551.2 |
| D-Leu | | 534.26 | 535.3 |
| Leu | Lys | 662.36 | 663.3 |
| Leu | Glu | 663.30 | 664.2 |
| Leu | Leu | 647.35 | 648.2 |
| D-Leu | D-Lys | 662.36 | 663.7 |

TABLE I-continued (IV)

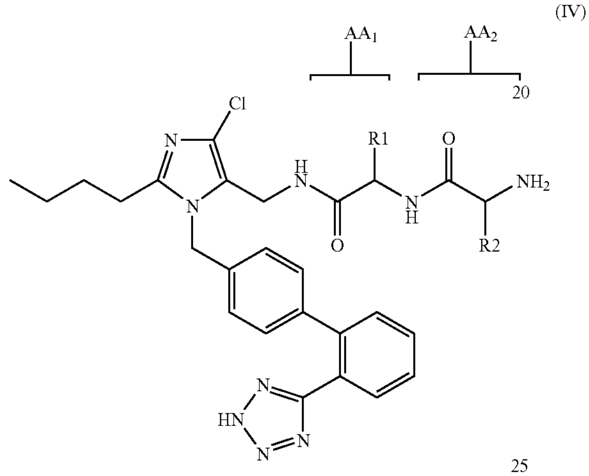

| AA1 | AA2 | MW (exact) | $MH^+$ observed |
|---|---|---|---|
| D-Leu | D-Glu | 663.30 | 664.6 |
| D-Leu | D-Leu | 647.35 | 648.7 |
| Leu | D-Leu | 647.35 | 648.7 |
| D-Leu | Leu | 647.35 | 648.7 |
| Phe | | 568.25 | 569.7 |
| NaI | | 618.26 | 619.6 |
| Cha | | 574.29 | 575.7 |

Examples 19-46

Losartan-Leu Derivatives Comprising a Resorter Moiety

Compounds of the general formula (V) are listed in Table 2 and were synthesised on solid support as described in Example 1. Biotin and fluorescein-NHS ester were purchased from Fluka and Pierce, respectively. In the cases where Tc chelate cPn216 is attached via a glutaryl linker three different synthetic methods were used. In most cases an active ester of formula (VI) was used. As an alternative the corresponding free acid was coupled using reagents like PyAOP or HATU, but in that case the coupling had to repeated several times. Also, the glutaryl-cPn216 moiety was attached in a two step reaction, as described for the corresponding diglycoloyl derivative in Example 1, by first reacting the resin with glutaric anhydride and in a subsequent step activate the resin bound carboxylic acid and couple cPn216 as the free amine of formula (VII). For synthesis of compounds containing the tetraamine chelate the fully Boc-protected building block (VIII) (GB 0416062.8) was used. The products were purified by reverse phase chromatography (Phenomenex Luna C18(2) columns) using suitable gradients of acetonitrile/water containing 0.1% TFA or formic acid and were analysed by LC-MS using electrospray ionisation.

TABLE 2
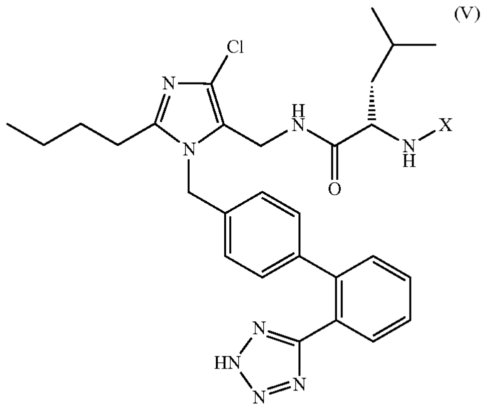
(V)
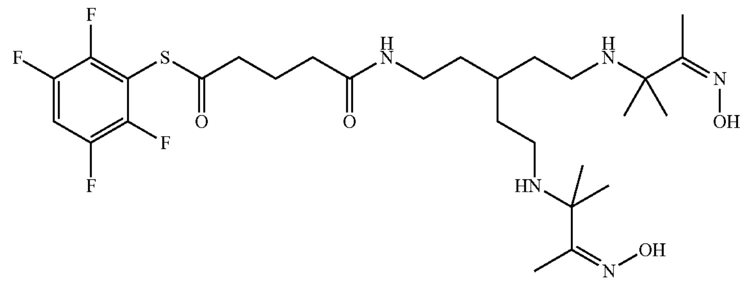
(VI)
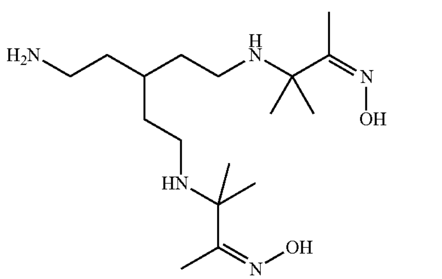
(VII)
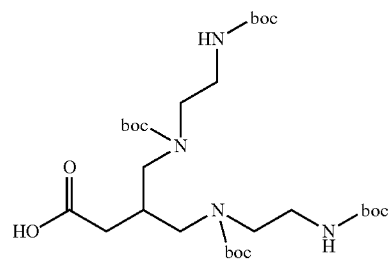
(VIII)
| X | Abbr | MW (exact) | MH+ obs. |
|---|---|---|---|
| 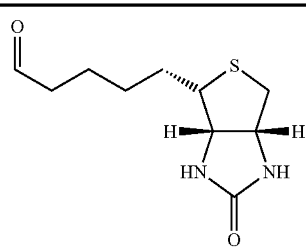 | Losartan-Leu-Biotin | 760.34 | 761.6 |

TABLE 2-continued
| | | | |
|---|---|---|---|
| 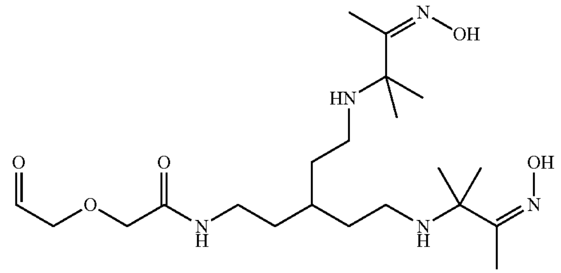 | Losartan-Leu-Diglycoloyl-cPn216 | 975.56 | 975.9 |
| 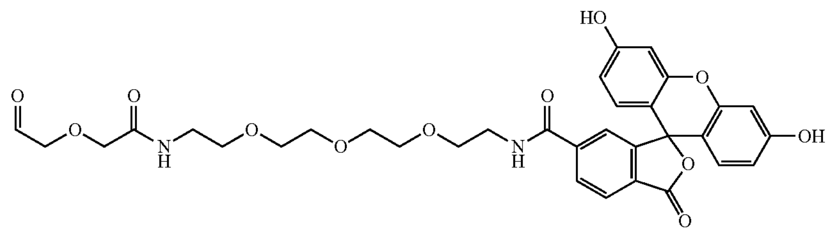 | Losartan-Leu-Diglycoloyl-PEG(4)-Fluorescein | 1182.46 | 1183.4 |
| 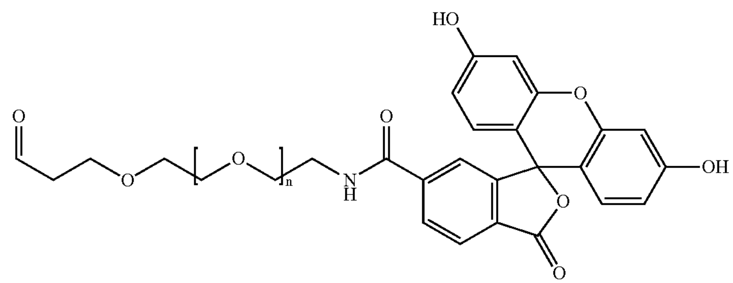 | Losartan-Leu-Propionyl-PEG(12)-Fluorescein | 1491.66 | 1492.6 |
| 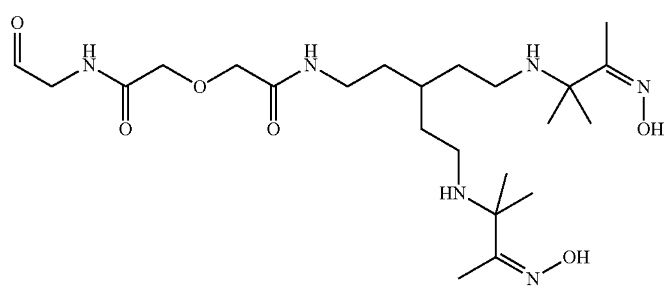 | Losartan-Leu-Gly-Diglycoloyl-cPn216 | 1032.58 | 1033.7 |

TABLE 2-continued
| | | | |
|---|---|---|---|
| 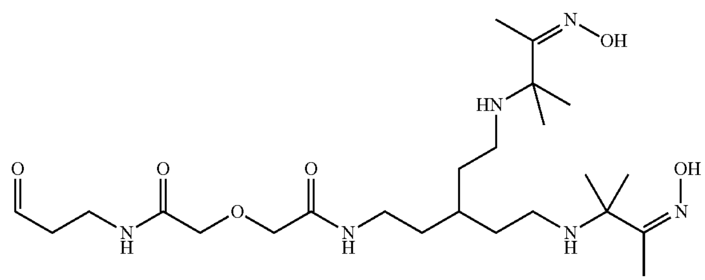 | Losartan-Leu-β-Ala-Diglycoloyl-cPn216 | 1046.59 | 1047.5 |
| 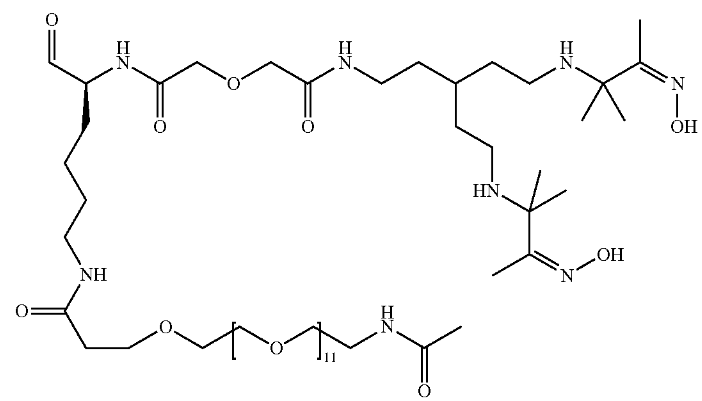 | Losartan-Leu-Lys(Propionyl-PEG(12)-Ac)-Diglycoloyl-cPn216 | 1745.01 | 1745.6 |

TABLE 2-continued
| | | | |
|---|---|---|---|
| 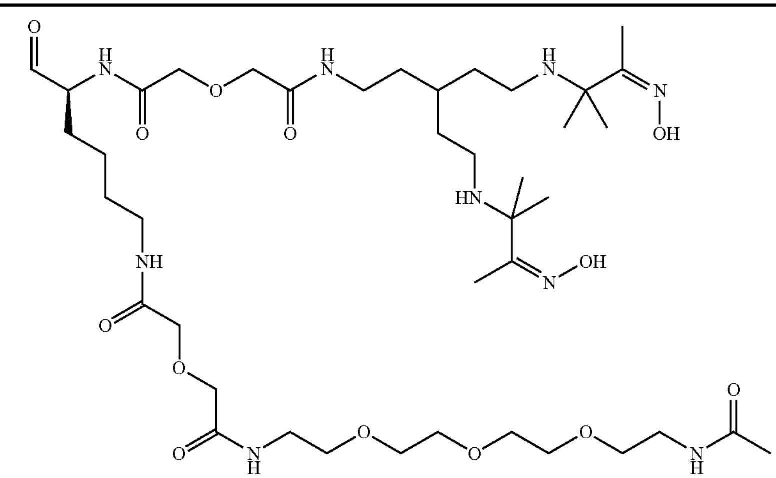 | Losartan-Leu-Lys(Diglycoloyl-PEG(4)-Ac)-Diglycoloyl-cPn216 | 1435.81 | 719.1 ($MH_2^{2+}$) |
| 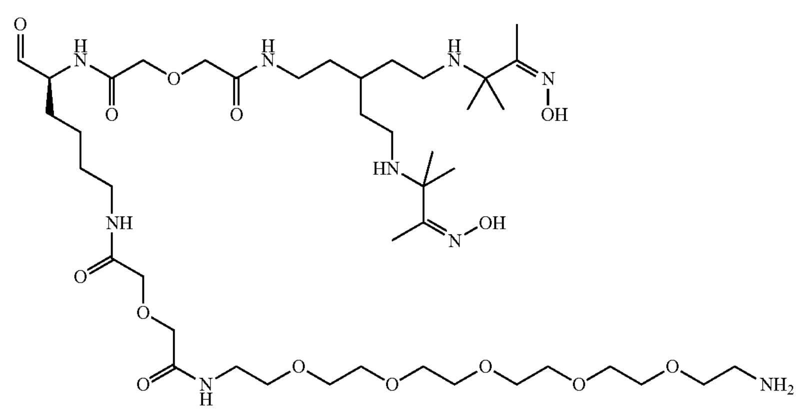 | Losartan-Lys(Diglycoloyl-PEG(6)-NH2)-Diglycoloyl-cPn216 | 1481.85 | 742.1 ($MH_2^{2+}$) |

TABLE 2-continued
| | | | |
|---|---|---|---|
| 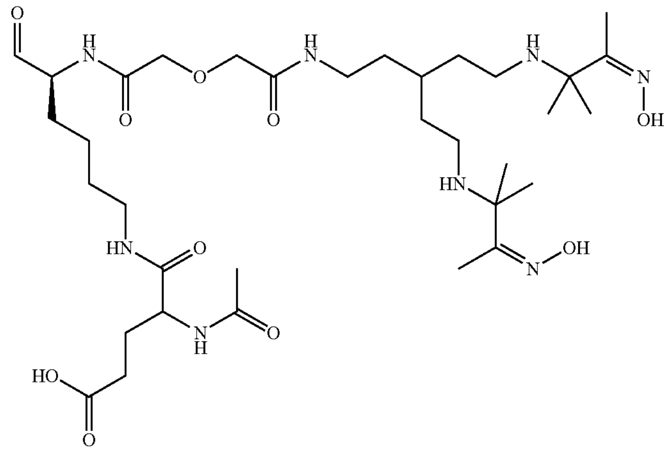 | Losartan-Leu-Lys(Glu-Ac)-Diglycoloyl-cPn216 | 1274.71 | 1275.5 |
| 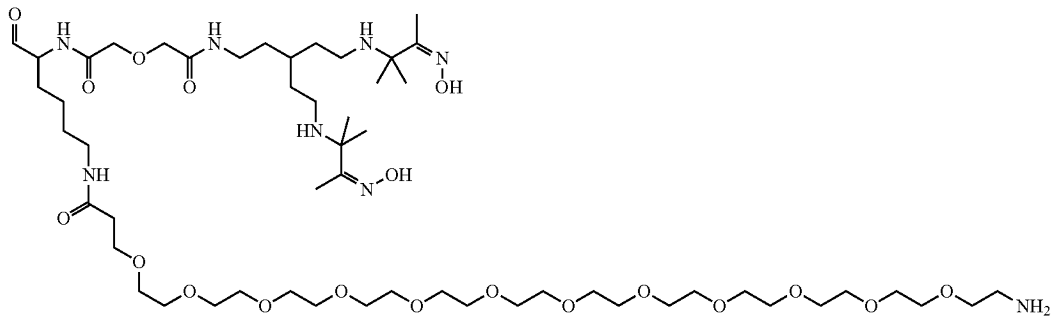 | Losartan-Leu-Lys(Propionyl-PEG(12)-NH2)-Diglycoloyl-cPn216 | 1703.00 | 852.6 ($MH_2^{2+}$) |
| 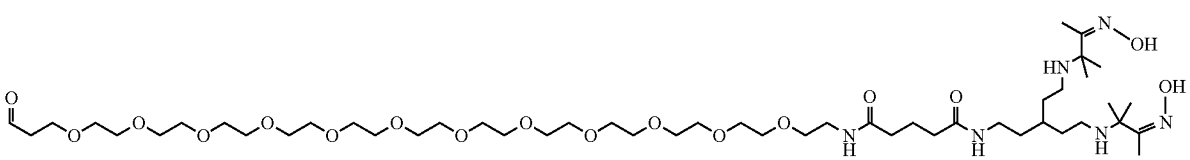 | Losartan-Leu-Propionyl-PEG(12)-Glutaryl-cPn216 | 1572.93 | 787.6 ($MH_2^{2+}$) |

TABLE 2-continued
| | | | |
|---|---|---|---|
| 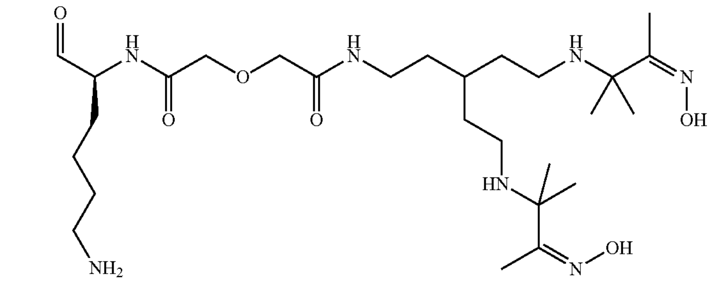 | Losartan-Leu-Lys-Diglycoloyl-cPn216 | 1103.65 | 552.4 ($MH_2^{2+}$) |
| 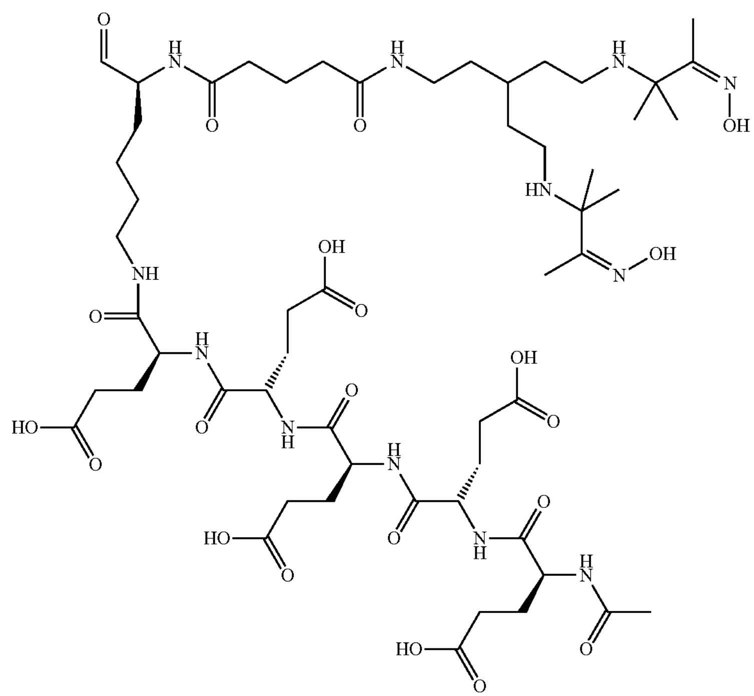 | Losartan-Leu-Lys($Glu_5$-Ac)-Glutaryl-cPn216 | 1788.90 | 895.9 ($MH_2^{2+}$) |

TABLE 2-continued
| | | | |
|---|---|---|---|
| 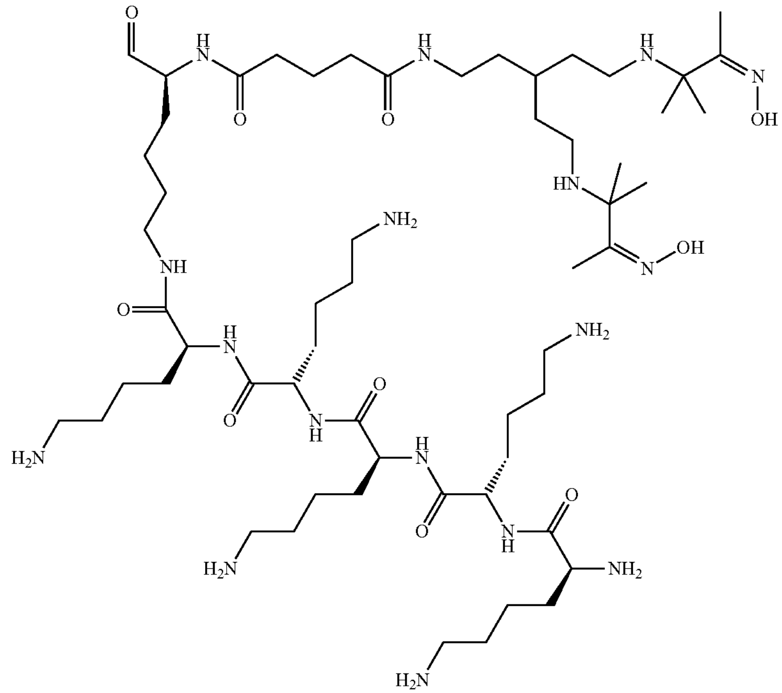 | Losartan-Leu-Lys (Lys$_5$)-Glutaryl-cPn216 | 1742.15 | 872.5 ($MH_2^{2+}$) |
| 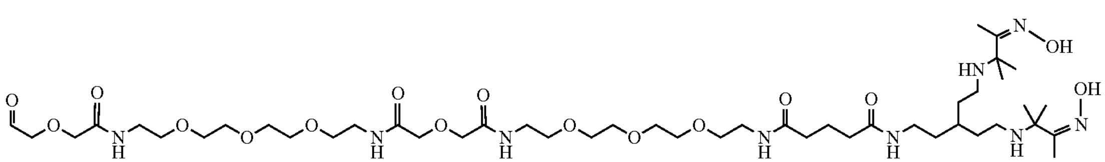 | Losartan-Leu-[Diglycoloyl-PEG(4)]2-Glutaryl-cPn216 | 1553.87 | 778.1 ($MH_2^{2+}$) |

TABLE 2-continued
| | | | |
|---|---|---|---|
| 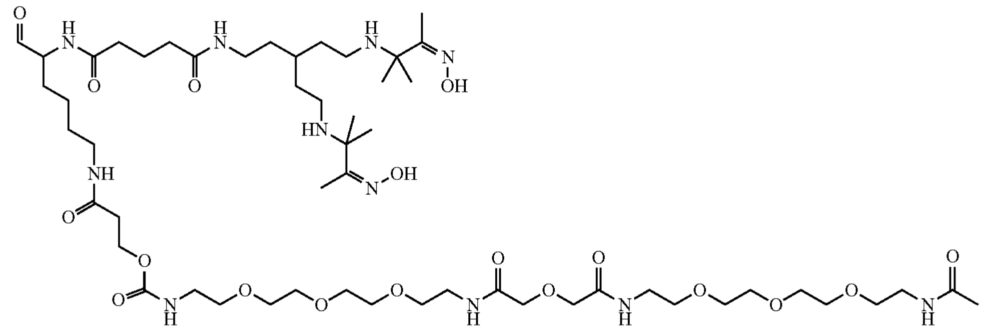 | Losartan-Leu-Lys([Diglycoloyl-PEG(4)]2-Ac)-Glutaryl-cPn216 | 1723.98 | 863.2 ($MH_2^{2+}$) |
| 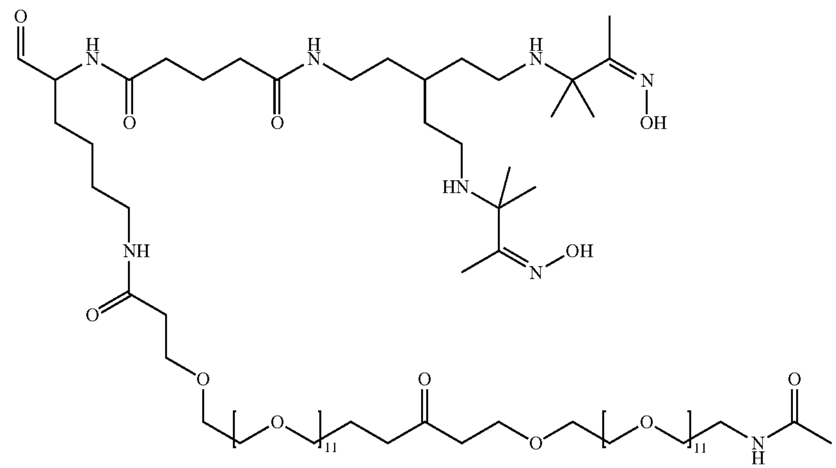 | Losartan-Leu-Lys([Propionyl-PEG(12)]2-Ac)-Glutaryl-cPn216 | 2342.39 | 1172.9 ($MH_2^{2+}$) |
| 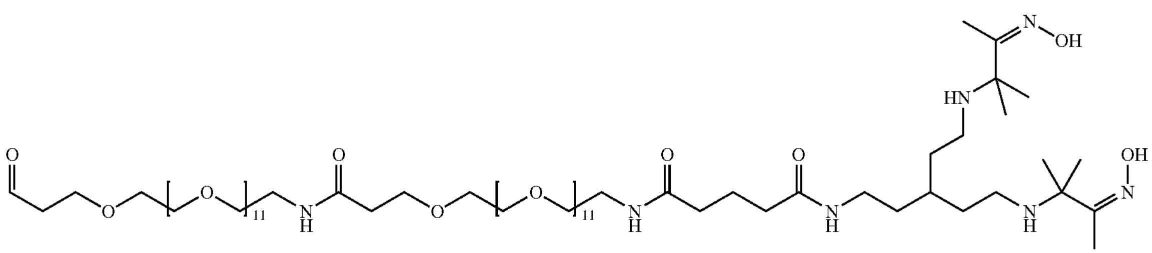 | Losartan-Leu-[Propionyl-PEG(12)]2-Glutaryl-cPn216 | 2172.28 | 1087.2 ($MH_2^{2+}$) |

TABLE 2-continued
| | | | |
|---|---|---|---|
| 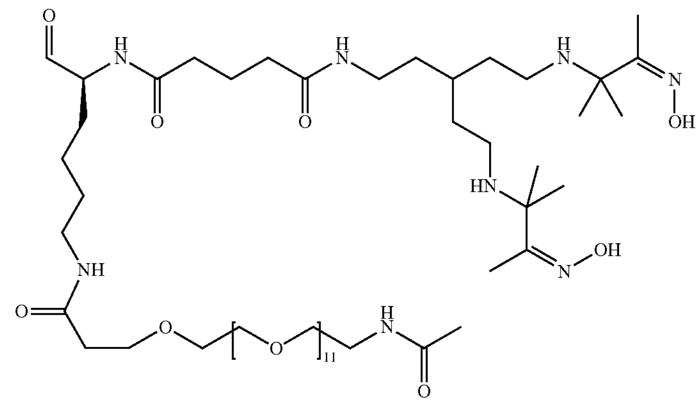 | Los-Leu-Lys(Propionyl-PEG12-Ac)-Glutaryl-cPn216 | 1743.04 | 1743.7 |
| 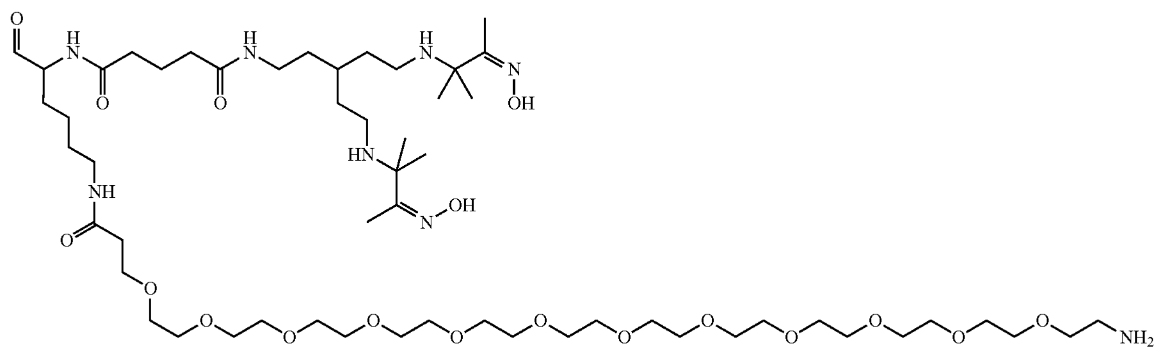 | Losartan-Leu-Lys(Propionyl-PEG(12)-NH2)-Glutaryl-cPn216 | 1701.02 | 852.0 ($MH_2^{2+}$) |
| 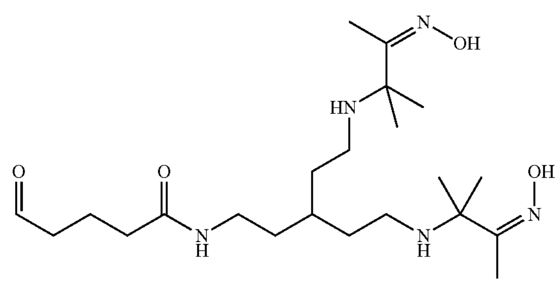 | Losartan-Leu-Glutaryl-cPn216 | 973.58 | 974.5 |

TABLE 2-continued
| | | | |
|---|---|---|---|
| 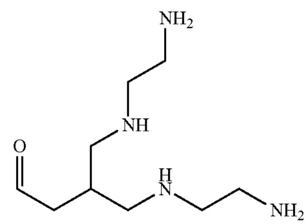 | Los-Leu-Tetraamine | 734.43 | 735.5 |
| 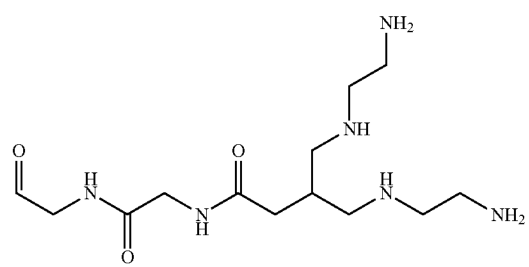 | Los-Leu-Gly-Tetraamine | 848.47 | 849.3 |
| 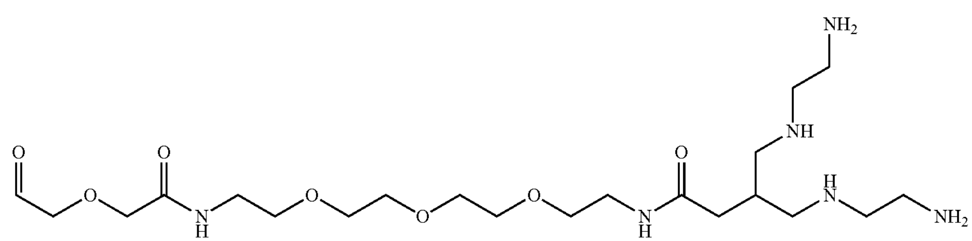 | Losartan-Leu-Diglycoloyl-PEG(4)-Tetraamine | 1024.57 | 1025.5 |

TABLE 2-continued
| | | | |
|---|---|---|---|
| 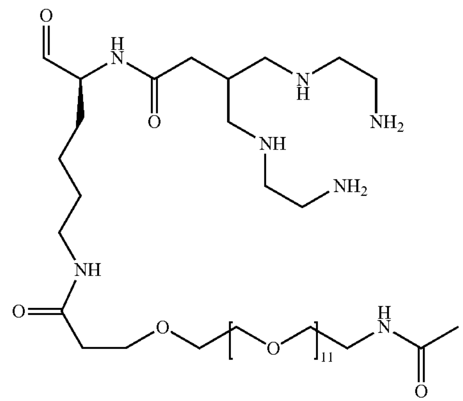 | Los-Leu-Lys(Propionyl-PEG12-Ac)-Tetraamine | 1503.88 | 1504.7 |
| 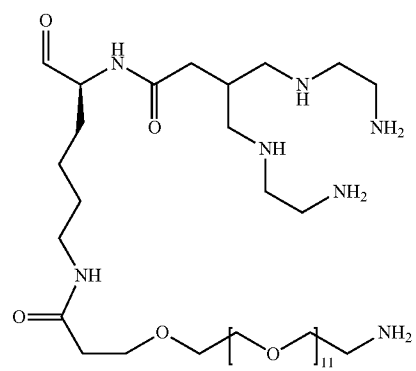 | Losartan-Leu-Lys(Propionyl-PEG(12)-NH2)-Tetraamine | 1461.87 | 1462.7 |
| 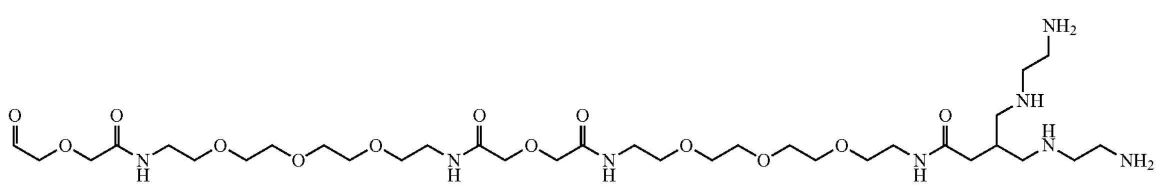 | Losartan-Leu-Lys-[Diglycoloyl-PEG(4)]2-Tetraamine | 1314.72 | 658.7 ($MH_2^{2+}$) |

What is claimed is:

1. A contrast agent which is $^{99m}$Tc (Losartan-Leu-diglycolyl-cPn216), $^{99m}$Tc (Losartan-Leu-Gly-diglycolyl-cPn216), $^{99m}$Tc (Losartan-Leu-β-Ala-diglycolyl-cPn216) or $^{99m}$Tc (Losartan-Leu-Lys(Propionyl-PEG(12)-Ac)-Diglycoloyl-cPn216).

2. A pharmaceutical composition comprising an effective amount of a contrast agent of claim 1 or a salt thereof, together with one or more pharmaceutically acceptable adjuvants, excipients or diluents for use in enhancing image contrast in in vivo imaging.

3. A method of generating enhanced images of a human or animal body previously administered with a contrast agent composition comprising a contrast agent of claim 1, which method comprises generating an image of at least part of said body.

* * * * *